United States Patent
Li

(10) Patent No.: US 12,156,957 B2
(45) Date of Patent: *Dec. 3, 2024

(54) SCENTED ELECTRONIC CANDLE

(71) Applicant: L&L Candle Company, LLC, Brea, CA (US)

(72) Inventor: Xiaofeng Li, Shenzhen (CN)

(73) Assignee: L&L Candle Company, LLC, Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,159

(22) Filed: Oct. 31, 2022

(65) Prior Publication Data

US 2023/0124562 A1 Apr. 20, 2023

Related U.S. Application Data

(63) Continuation of application No. 17/121,152, filed on Dec. 14, 2020, now Pat. No. 11,484,617.

(30) Foreign Application Priority Data

Dec. 17, 2019 (CN) .......................... 201922274189.4

(51) Int. Cl.
*A61L 9/03* (2006.01)
*A61L 9/12* (2006.01)
(Continued)

(52) U.S. Cl.
CPC ............. *A61L 9/037* (2013.01); *F21S 8/035* (2013.01); *F21S 10/046* (2013.01); *A61L 9/127* (2013.01);
(Continued)

(58) Field of Classification Search
None
See application file for complete search history.

(56) References Cited

U.S. PATENT DOCUMENTS

| 5,622,424 A | 4/1997 | Brady |
| 9,810,388 B1 | 11/2017 | Li |

(Continued)

FOREIGN PATENT DOCUMENTS

| CN | 109185823 A | 1/2019 |
| KR | 10-2005-0057630 A | 6/2005 |
| KR | 10-2016-0122055 A | 10/2016 |

OTHER PUBLICATIONS

First Examination Report for Australian Patent Application No. 2020404865, mailed May 11, 2023 (5 pages).

(Continued)

*Primary Examiner* — Alan B Cariaso
(74) *Attorney, Agent, or Firm* — Perkins Coie LLP

(57) ABSTRACT

Methods, systems and devices associated with a scented electronic candle are described. In one example, an electronic candle includes an outer shell with one or more openings configured to allow a fragrance to exit to an ambient environment of the electronic candle. The outer shell comprises a central opening such that a flame element protrudes at least partially through the central opening. The device includes a light emitting component to emit a light onto the movable flame, and a mounting base positioned below the movable flame element. The device also includes a scent storage component removably coupled to the mounting base. The scent storage component includes a container to store a fragrance and an absorption member configured to draw the fragrance to the ambient environment of the electronic candle through the one or more small openings of the outer shell.

10 Claims, 14 Drawing Sheets

(51) Int. Cl.
    *F21S 8/00*        (2006.01)
    *F21S 10/04*      (2006.01)
    *F21Y 115/10*    (2016.01)

(52) U.S. Cl.
    CPC ........ *A61L 2209/11* (2013.01); *A61L 2209/12* (2013.01); *A61L 2209/133* (2013.01); *A61L 2209/15* (2013.01); *F21Y 2115/10* (2016.08)

(56) References Cited

U.S. PATENT DOCUMENTS

| | | | |
|---|---|---|---|
| 10,010,640 | B1 | 7/2018 | Li |
| 10,251,967 | B1 | 4/2019 | Wang |
| 11,484,617 | B2 * | 11/2022 | Li .......................... F21S 8/035 |
| 2005/0169666 | A1 | 8/2005 | Porchia et al. |
| 2005/0247802 | A1 | 11/2005 | Varanasi et al. |
| 2007/0253222 | A1 | 11/2007 | Driska et al. |
| 2008/0068822 | A1 * | 3/2008 | Spartano ............. H01R 13/447 |
| | | | 362/95 |
| 2009/0310374 | A1 | 12/2009 | Lederer |
| 2011/0019422 | A1 * | 1/2011 | Schnuckle ............. F21S 10/04 |
| | | | 362/277 |
| 2013/0182446 | A1 * | 7/2013 | Gourdie ................... B44F 1/06 |
| | | | 156/247 |
| 2016/0195257 | A1 | 7/2016 | Hsiao |
| 2017/0067625 | A1 * | 3/2017 | Edgar ..................... F21S 6/002 |
| 2017/0167677 | A1 | 6/2017 | Patton et al. |
| 2017/0368219 | A1 * | 12/2017 | Li .......................... A61L 9/032 |
| 2018/0283634 | A1 * | 10/2018 | Ding ...................... H05B 45/20 |
| 2018/0292058 | A1 * | 10/2018 | Li ............................. A61L 9/03 |
| 2018/0361005 | A1 | 12/2018 | Li |
| 2019/0195447 | A1 * | 6/2019 | Wu ........................... B05B 1/14 |
| 2019/0275187 | A1 | 9/2019 | Hsiao |
| 2019/0275188 | A1 | 9/2019 | Hsiao |
| 2021/0178003 | A1 | 6/2021 | Li |

OTHER PUBLICATIONS

Notice of Reasons for Rejections for Japanese Patent Application No. 2022-533140, mailed May 9, 2023 (17 pages).

International Search Report and Written Opinion for International Patent Application No. PCT/US2020/064878, mailed Mar. 30, 2021.

Extended European Search Report for European Patent Application No. 20903530.2, mailed Dec. 12, 2023 (10 pages).

* cited by examiner

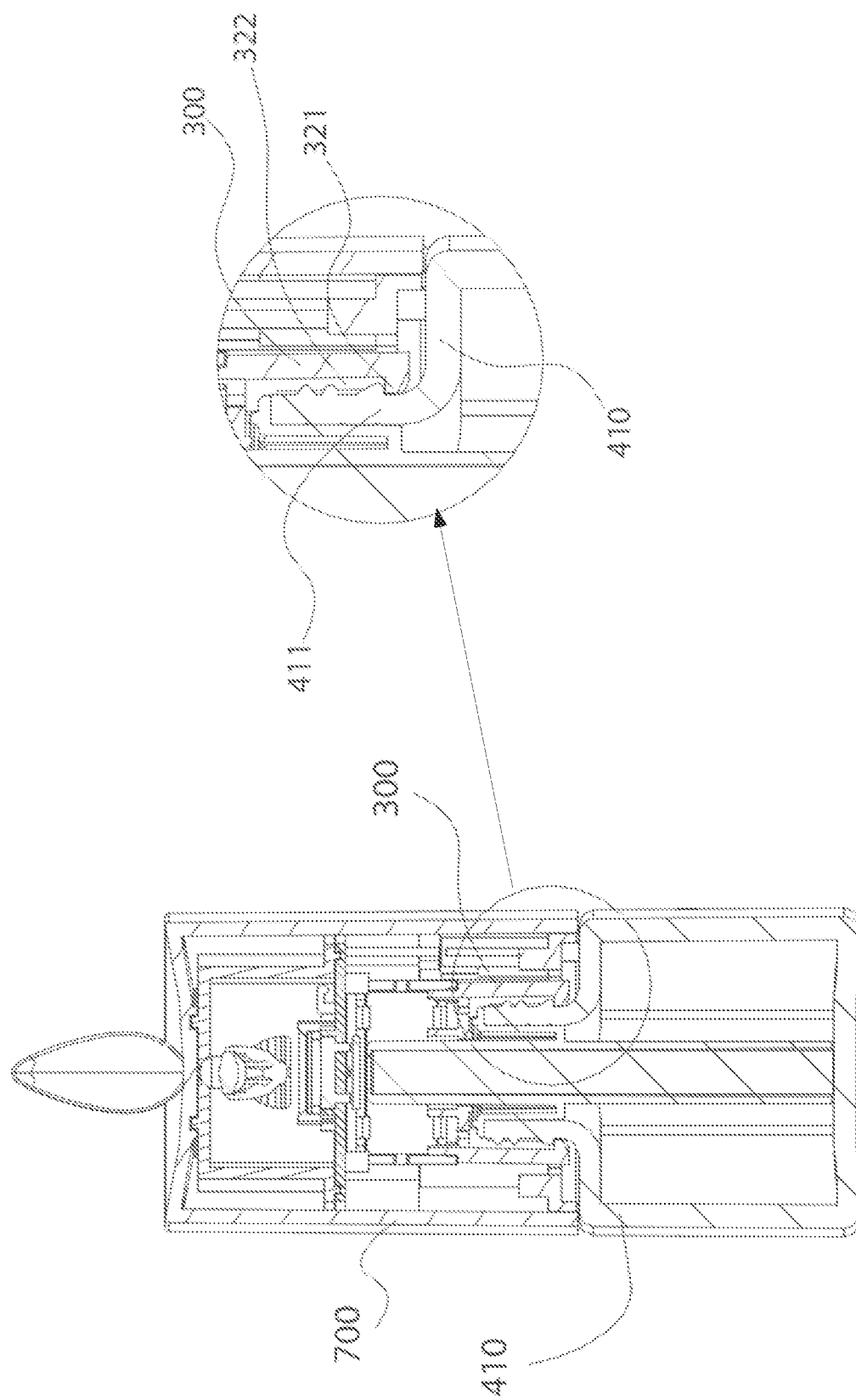

SCENTED ELECTRONIC CANDLE

CROSS-REFERENCE TO RELATED APPLICATION(S)

This patent document is a continuation of U.S. patent application Ser. No. 17/121,152, filed Dec. 14, 2020, which further claims priority to Chinese Patent Application No. 201922274189.4, filed Dec. 17, 2019. The entire content of the before mentioned patent applications is incorporated by reference in this patent document.

TECHNICAL FIELD

The present disclosure relates to electronic lighting technology, and more particularly, to a scented electronic candle device.

BACKGROUND

In home facilities, public restaurants, churches, temples, large theme parks or urban public infrastructures, candles are used to provide lighting and to create ceremonial or romantic atmospheres. However, a conventional candle has a short lifetime and needs to be replaced frequently. Moreover, a potential risk of fire due to the fire flame prevents candles from being widely used.

SUMMARY

The present disclosure relates to scented electronic candles that, among other features and benefits, provide rich visual and olfactory experiences to users.

In one example aspect, an electronic candle is disclosed. The electronic candle includes an outer shell comprising one or more small openings configured to allow a fragrance to exit to an ambient environment of the electronic candle. The outer shell further comprising a central opening that allows a flame element to protrude at least partially through the central opening of the outer shell. The flame element is supported by a support structure to allow movement of the flame element that mimics a real flame. The device includes a light emitting component positioned at an angle with respect to the movable flame element to emit a light onto the movable flame and a mounting base positioned below the movable flame element and the light emitting component. The light emitting component and at least part of the mounting base are enclosed by the outer shell. The device also includes a scent storage component removably coupled to the mounting base. The scent storage component comprises a container to store a fragrance and an absorption member configured to draw the fragrance from the container to the ambient environment of the electronic candle through the mounting base and the one or more small openings of the outer shell.

These, and other, aspects are described in the present document.

BRIEF DESCRIPTION OF THE DRAWINGS

FIG. 6 illustrates a cross section of a fragrance diffuser bottle in accordance with the present technology.

FIG. 7 illustrates selected components of the fragrance diffuser bottle shown in FIG. 6 bottle in accordance with the present technology.

DETAILED DESCRIPTION

Figure 1:
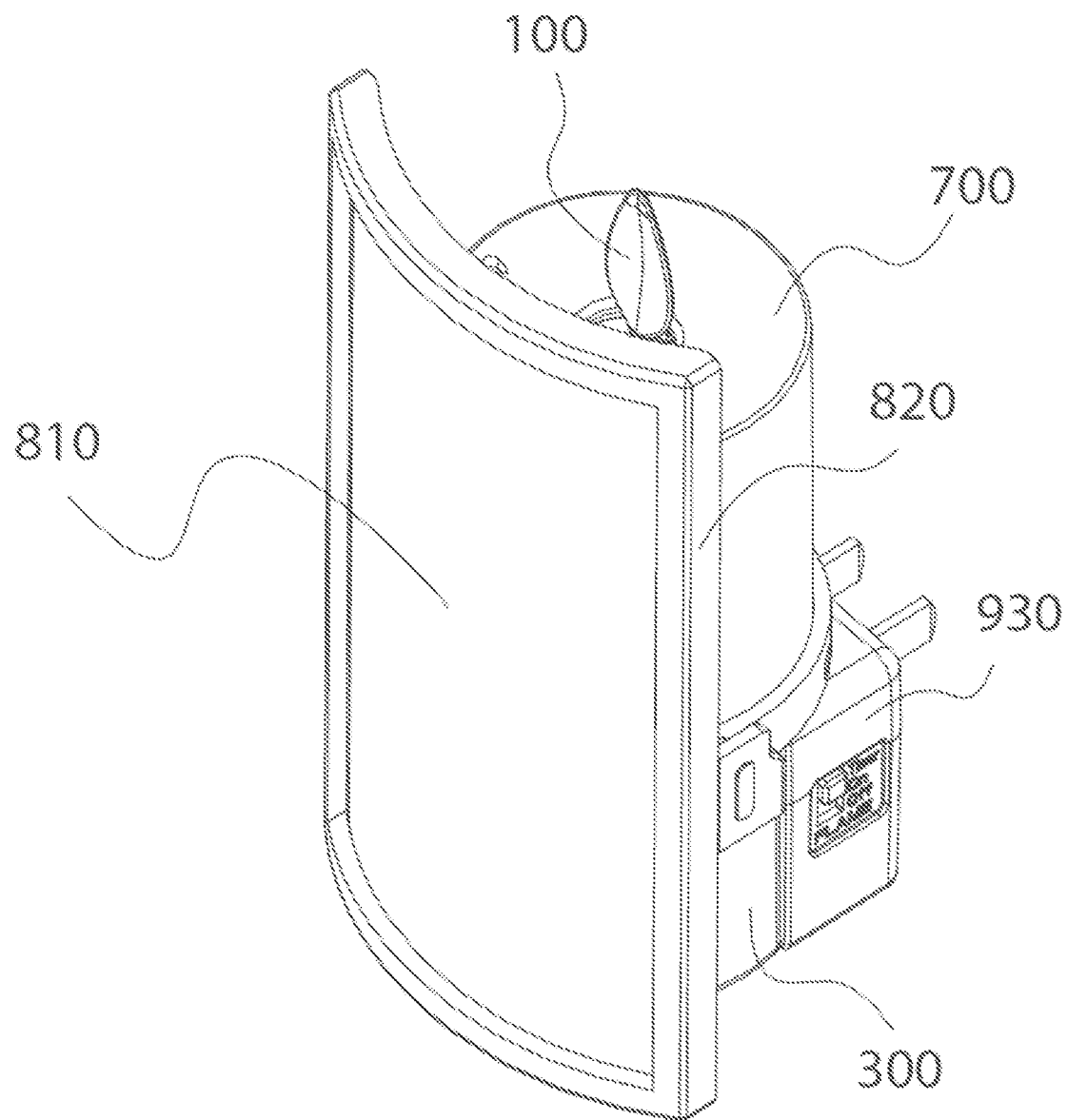
FIG. 1 illustrates an example electronic candle with a sheet attached thereto in accordance with the present technology.

In order to facilitate the understanding of the features and advantages of the disclosed technology, the present disclosure will be explained with reference to the example figures and embodiments. It is to be noted here that the embodiments and features can be combined with each other, provided that they do not conflict. Thus, the scope of the present disclosure is not limited to the embodiments disclosed below.

With the development of new technologies, electronic candles now can provide illumination similar to real candles and also possess aesthetic and decorative qualities, which has let to their wide-ranging uses in hotels, churches and homes. In particular, scented electronic candles, configured to release various types of fragrances while emitting light, provide a combination of aromatherapy and rich visual experiences for users. This patent document discloses techniques that can be implemented in various embodiments to provide aesthetically pleasing scented electronic candles that operate effectively and safely in diffusing fragrances.

FIGS. 1-5B illustrate embodiments of scented electronic candles in accordance with the present technology. A scented electronic candle in accordance with the present technology can include the following components: an outer shell 700 (see FIGS. 1-2), a flame sheet 100 (see FIGS. 1-2), a power plug assembly 930 (see FIGS. 1-2), a mounting base 300 (see FIGS. 3A-5B), a scent storage component 400 (see FIGS. 2-3), a light emitting unit 200 (see FIGS. 3A-4B), a heating unit 600 (see FIGS. 3A-4B), and a control unit such as a circuit board 1000 provided with a control circuit (see FIGS. 3A-4B).

Figure 2:
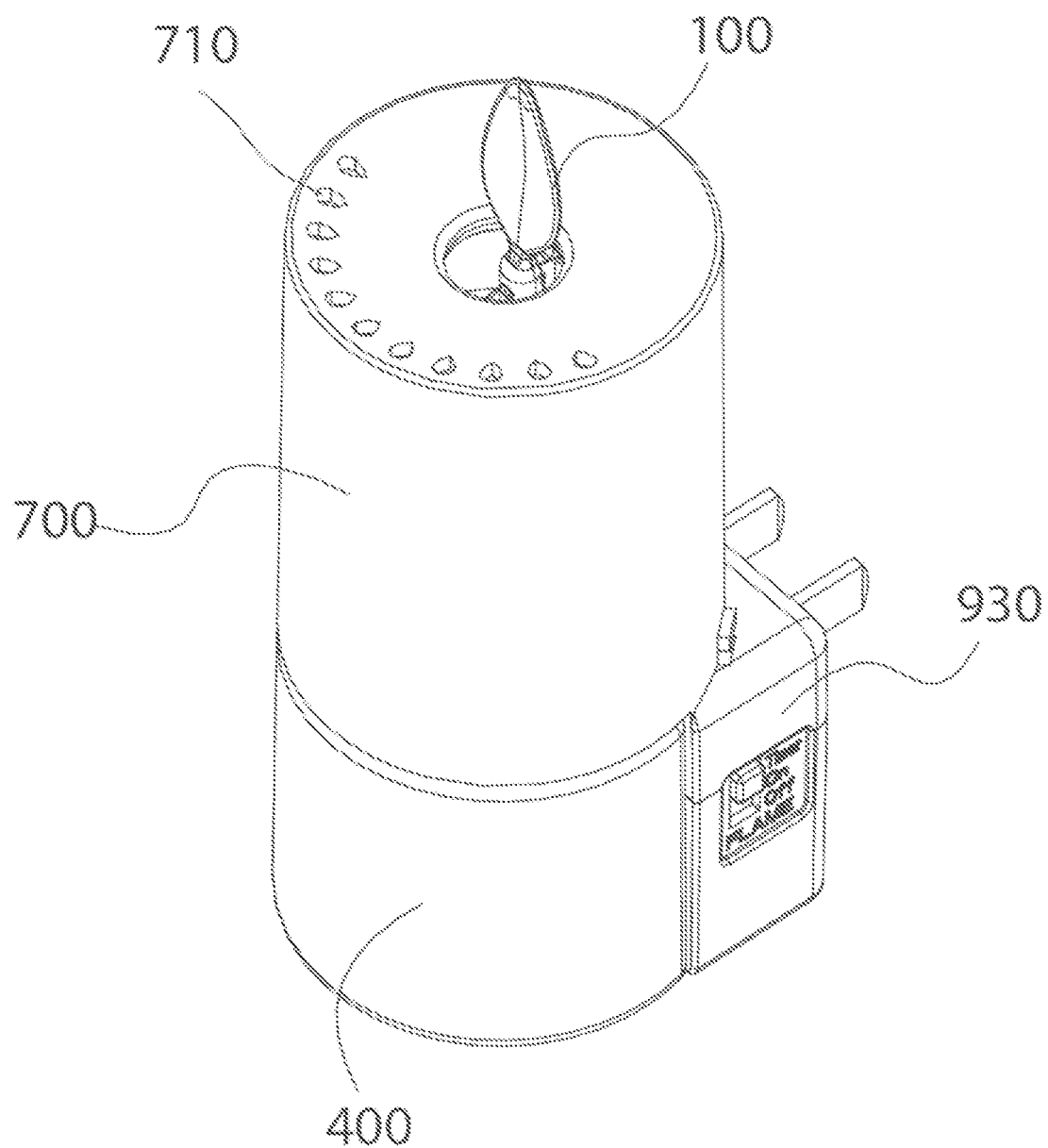
FIG. 2 illustrates another example electronic candle in accordance with the present technology.

As shown in FIGS. 1-2, the scented electronic candle includes an outer shell 700. The outer cylinder 700 can have a cylindrical structure and can be made of wax or other materials (such as plastic). The outer shell 700 is installed on a mounting base 300, which is coupled to a scent storage component 400. The top surface of the outer shell 700 includes one or more small openings 710 to allow the fragrance stored in the scent storage component 400 to diffuse into the ambient environment.

The scented electronic candle also includes a flame element 100. The flame element 100 can be partly or completely positioned outside the outer shell 700. Other components such as the light emitting unit 200, the heating unit 600, and the control unit can be arranged within the outer shell 700. In some embodiments, as shown in FIG. 1, part of the mounting base 300 is positioned within the outer shell 700 and part of the mounting base 300 (e.g., the base plate 391) is exposed. In some embodiments, as shown in FIG. 2, the outer shell 700 cover the mounting base 300 entirely such that the scented electronic candle device has a uniform shape mimicking a real candle.

Figure 3A:
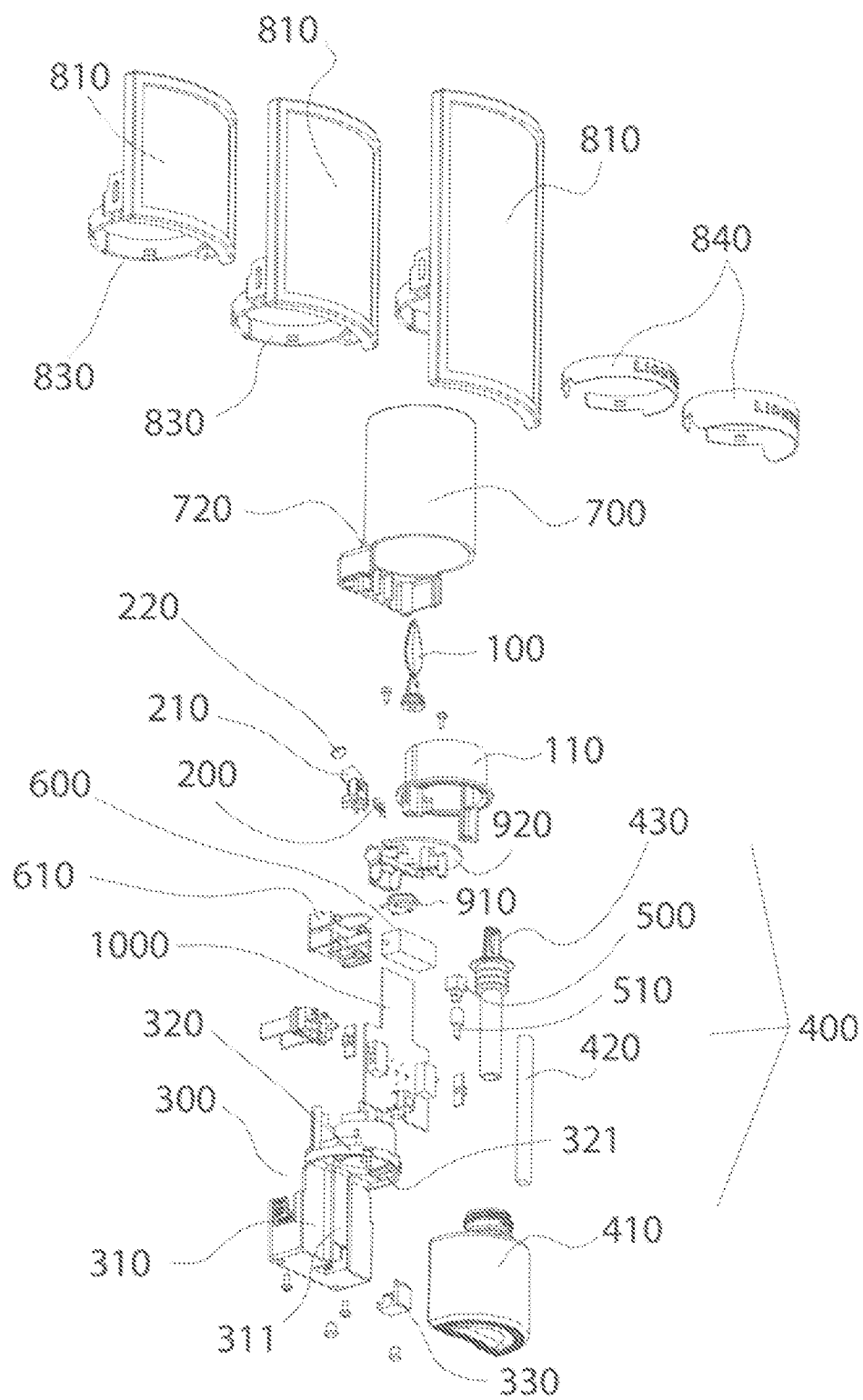
FIG. 3A illustrates a blow-up diagram of components of an example electronic candle shown in FIG. 1 in accordance with the present technology.
Figure 3B:
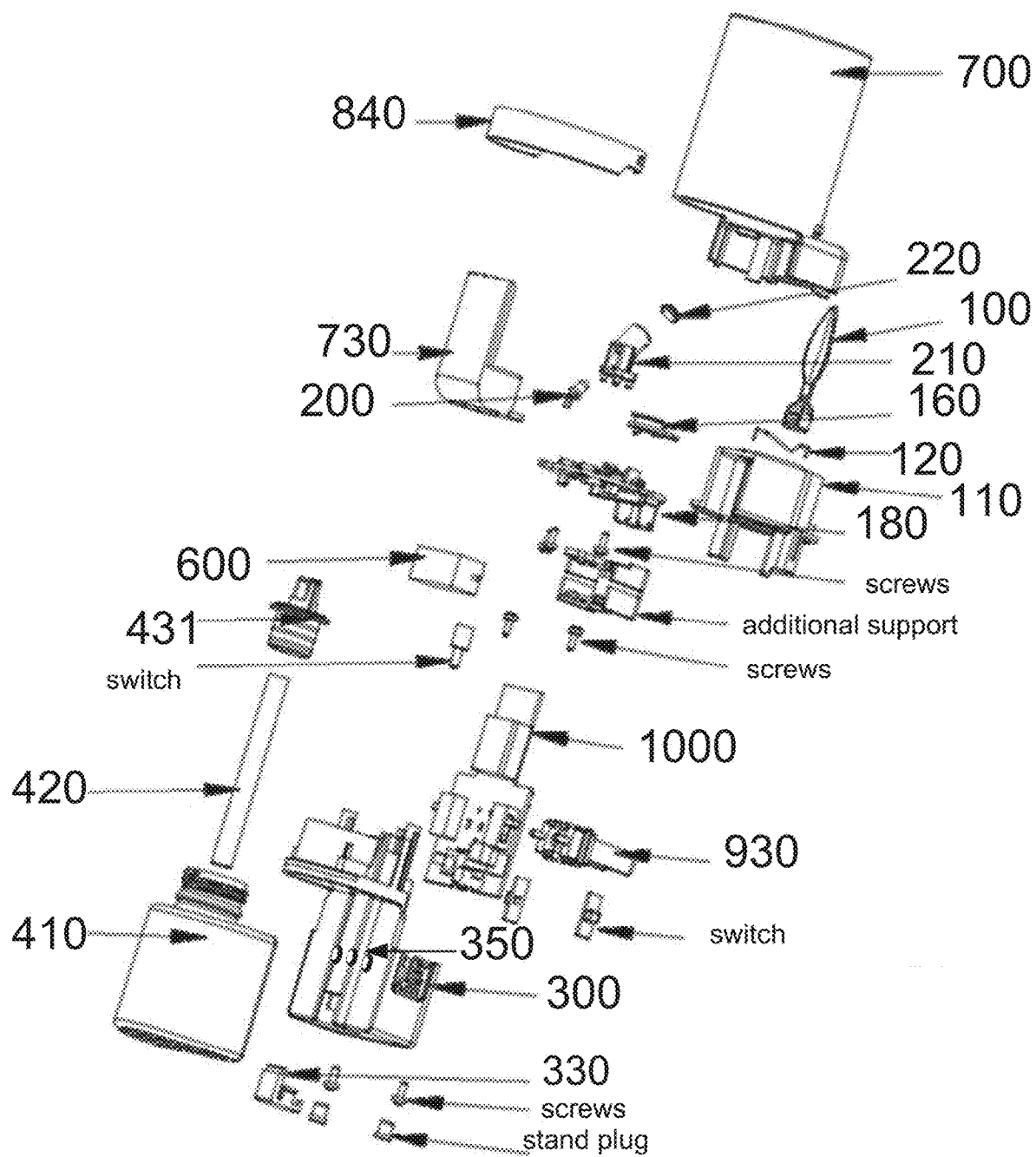
FIG. 3B illustrates a blow-up diagram of components of an example electronic candle shown in FIG. 2 in accordance with the present technology.
Figure 4A:
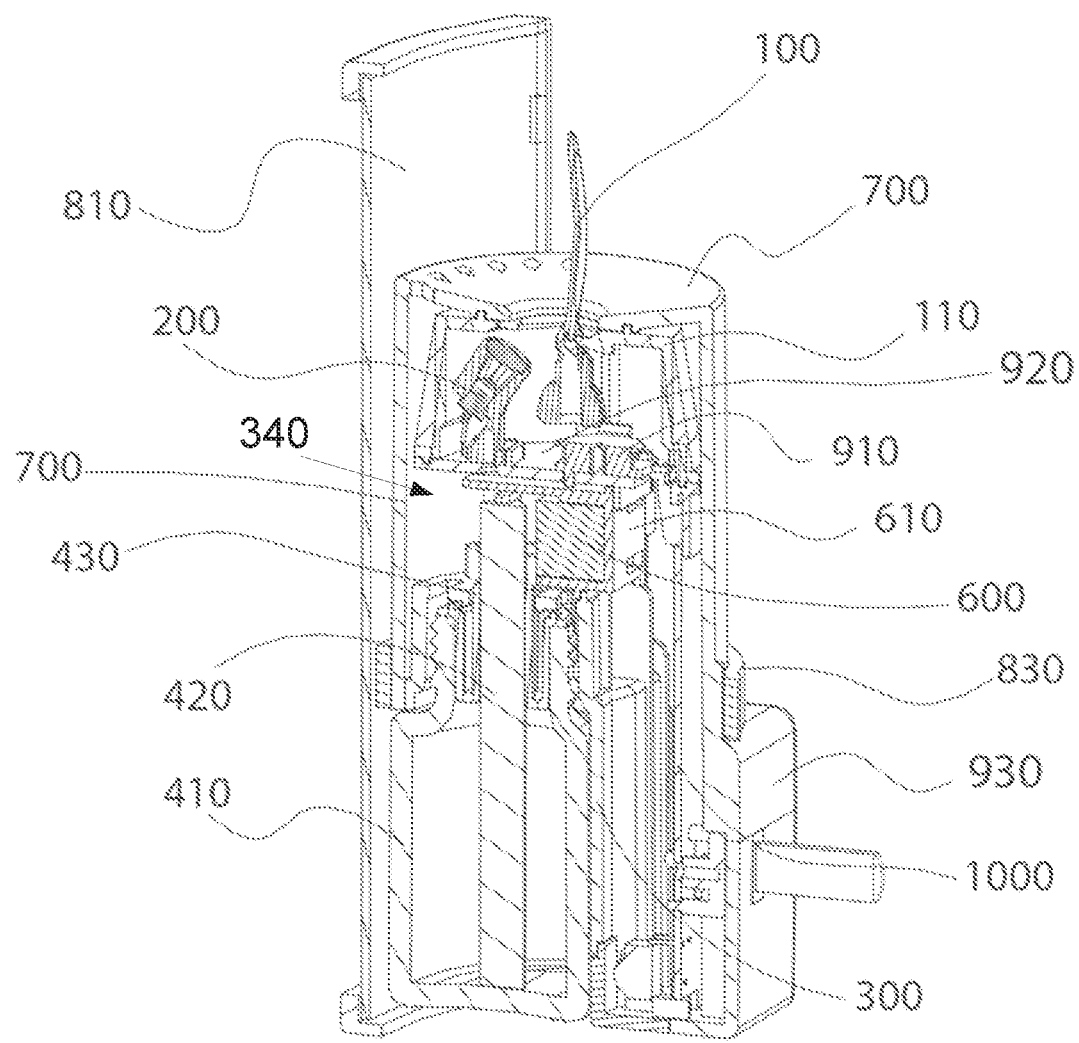
FIG. 4A illustrates a cross section of the example electronic candle shown in FIG. 3A in accordance with the present technology.
Figure 4B:
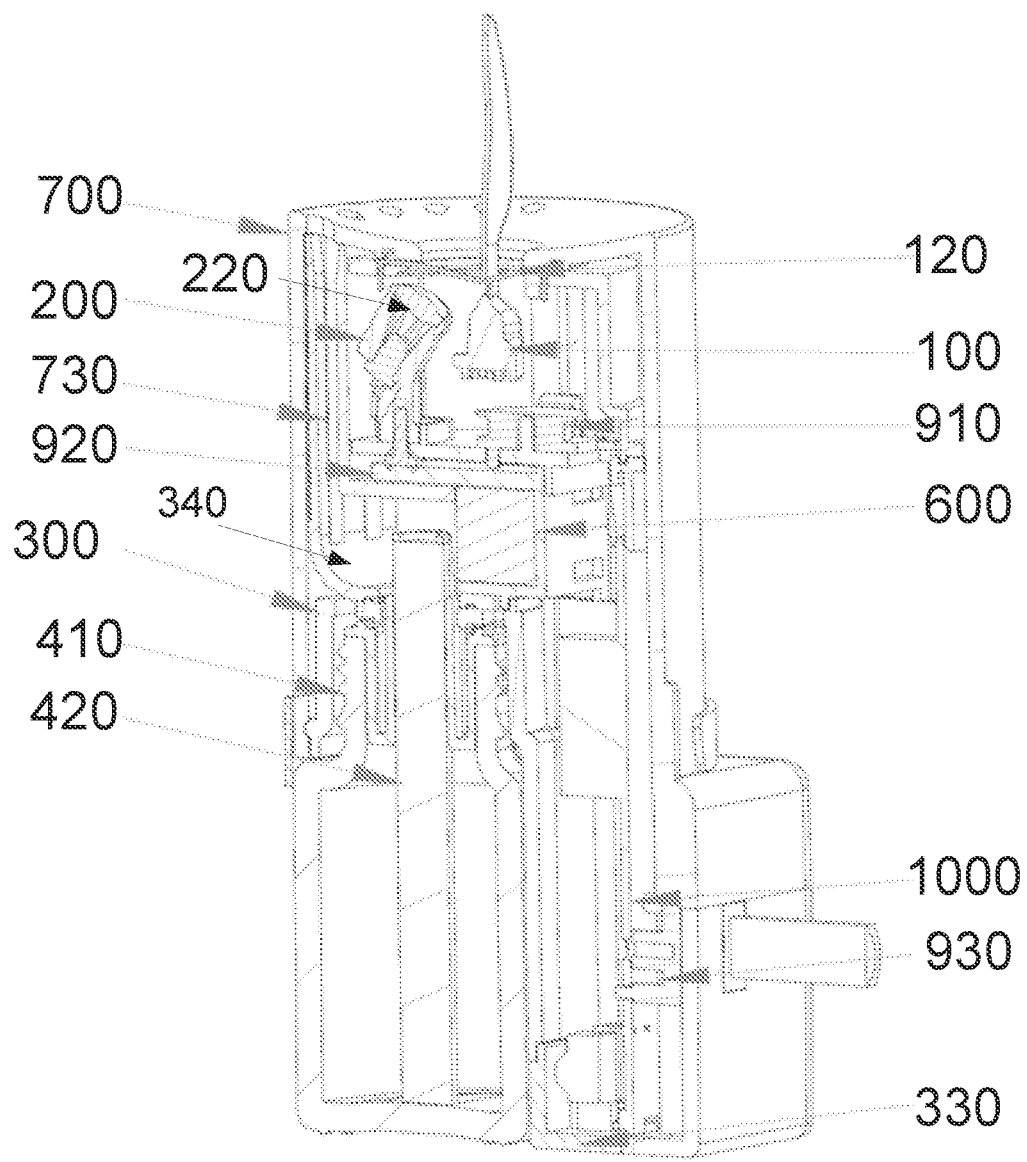
FIG. 4B illustrates a cross section of the example electronic candle shown in FIG. 3B in accordance with the present technology.

In some embodiments, the scented electronic candle device includes a top opening that allows a flame element 100 to protrude, at least partially, from the opening. The flame element 100 has a shape of a real flame. The flame element 100 can be a fixed element or a movable element that can swing freely to mimic the flickering movement of a real flame. In some embodiments, the flame element 100 can be fixedly or movably coupled on the mounting base 300. For example, as shown in FIG. 4A, the scented electronic candle device includes a support structure 110 (e.g., a hook bracket) that is mounted on the mounting base 300 to support a movable flame element 100. In some embodiments, as shown in FIG. 4B, the support structure 100 comprises a wire 120 positioned across the top opening to support the movable flame element 100. The wire 120 can be supported by a wire support 180 as shown in FIG. 3B. In some embodiments, a ring 160 can be positioned around the opening on a ring support 170. In some embodiments, the ring 160 can also operate as a touch sensitive on-off switch. In some embodiments, an additional metal plate can be positioned on or close to the ring support to operate as a touch sensitive on-off switch. The touch sensitive on-off switch can be made of conductive material that forms a capacitive element in electrical connection with the control circuit. When a user's finger contacts, or is within close proximity of, the touch sensitive on-off switch, a capacitive contact is formed to complete a circuit. The touch-sensitive mechanism can be used for turning the candle on or off, or for controlling other functions of the scented candle in a step-wise manner. For example, each touch can increase or decrease intensity of the light source, to switch the color of light, or to change a mode of operation (e.g., from flickering to constant intensity). In some embodiments, the touch sensitive element (shaped as a ring, or other shapes) includes two segments that are preferably poisoned at two different sides of the flame element on the top surface of the candle device. In such embodiments, the two-piece touch sensitive element is configured to operate as a switch (e.g., conduct a current) only if both segments of the touch sensitive element are touched. For example, a user can touch one segment of the touch sensitive element that is positioned close to, and on one side of, the flame element with his/her thumb, and the other segment of the touch sensitive element that is positioned close to, and on an opposite side of, the flame element with his/her index finger to activate the switch and turn off the imitation candle device. As such, the multi-segment touch element can be used to simulate the appearance that the user is extinguishing the candle flame using his/her fingers.

In some embodiments, the flame element 100 can include a magnet (e.g., at the lower end of the flame element). As shown in FIGS. 4A-B, the scented electronic candle device includes a magnetic coil 910 positioned below the flame element 100. The magnetic coil 910 is connected to the control unit 1000 can be connected to alter the generated magnetic field, thereby driving the movement of the flame element 100 to simulate the movement of a real flame. The magnetic coil 910 can be positioned in a coil holder 920 (as shown in FIG. 4B), which is installed on the mounting base 300 of the scented electronic candle device.

The scented electronic candle device includes a light emitting unit 200 that emits light onto the flame element 100. The light emitting unit 200 can include one or more light emitting diodes (LEDs). In some embodiments, the LEDs can emit light of different colors. In some embodiments, the light-emitting unit 200 is fixedly coupled to the mounting base 300. In some embodiments, the light-emitting unit 200 is movable with respect to the mounting base 300 and the flame element 100. For example, the light-emitting unit 200 can swing back and forth while the flame piece 100 is fixedly coupled to the mounting base 300. In some embodiments, the light-emitting unit 200 is positioned in a light-emitting unit holder 210 (as shown in FIGS. 3A-3B). The light-emitting unit holder 210 further provides a lens 220 positioned between the one or more LEDs and the flame element 100 to direct and focus the light emitted from the LEDs. The angle of the light cast by the light emitting unit 200, the relative movement between the light element 100 and the light emitting unit 200, and/or the combination of colors of the LEDs can form an effect that simulates a real flame.

In some embodiments, the scented candle device also includes a motion or acoustic sensor (e.g., a microphone) that is held in place within the interior of the candle device. The sensor converts motion and/or acoustic signals into electrical signals that are provided to the control circuit. For example, a microphone can be positioned closer to the top surface of the scented candle device to intercept sound waves that travel into the interior of the scented candle device. The central opening of the outer shell allows the microphone to capture acoustic waves that travel down into the interior of the scented candle device. In this way, when a user blows in the direction of the scented flame element 302, the blow is captured by the microphone, and the appropriate signals are generated to turn off the scented candle device.

The scented electronic candle device further includes a scent storage component 400 that can store various types of fragrances. The scent storage component 400 can be installed by connecting to a part of the mounting base 300 (e.g., coupled to the top part of the mounting base 300 and positioned against a side wall of the mounting base 300 as shown in FIGS. 4A-B). The fragrance stored in the scent storage component 400 can be in various forms, such as a solid form or a liquid form. In the examples illustrated in FIGS. 3A-5, the scent storage component 400 stores a liquid fragrance. The scent storage component 400 includes a fragrance container 410 for storing the liquid fragrance and a liquid absorption member 420.

In some embodiments, the fragrance container 410 can be a fragrance diffuser bottle. FIGS. 6-7 illustrate an example fragrance diffuser bottle in accordance with the present technology. The lower end of the liquid absorbing member 420 extends into the fragrance container 410, and the top end extends outside of the fragrance container 410. The liquid absorbing member 420 can include a material capable of absorbing liquid, such as a cotton wick or a woven felt wick, so as to deliver the fragrance in the fragrance container 410 to the outside of the fragrance container 410. In some embodiments, as shown in FIGS. 4A-B, the top end of the liquid absorbing member 420 extends into a chamber 340 formed within the mounting base 300 that is configured to guide the fragrance from the top end of the liquid absorbing member 420 to the openings on the outer shell 700. In some embodiments, as shown in FIG. 48, the side wall of chamber includes one or more guide tubes 730 (also shown in FIG. 3B) that are connected to the small openings 710 on the outer shell 700 to further facilitate the directing of the fragrance from the liquid absorbing member 420 to the ambient environment. The one or more guide tubes provide more efficient delivery of the fragrance to the ambient environment of the scented candle.

Figure 5A:
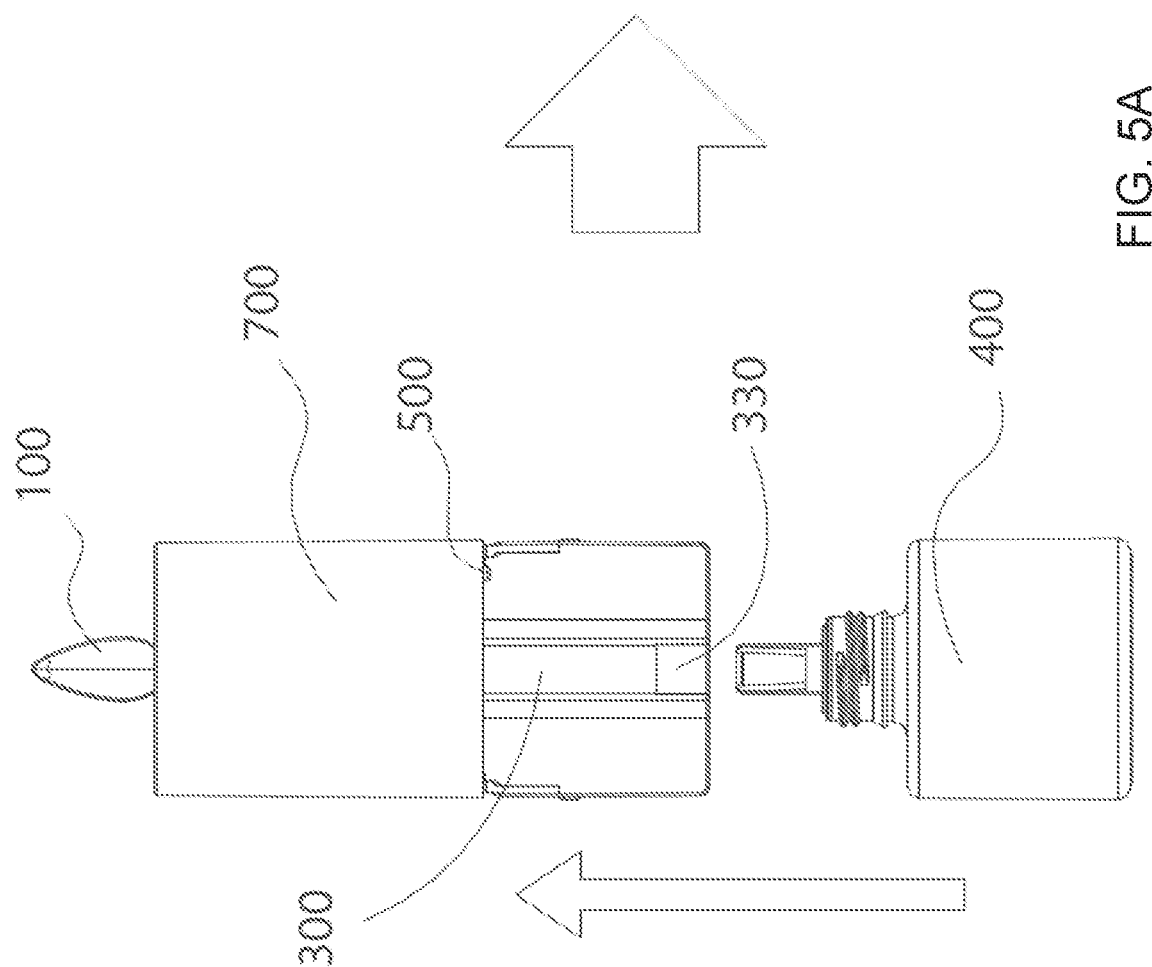
FIG. 5A illustrates an example installation process of installing a scent storage component of an example electronic candle in accordance with the present technology.
Figure 5B:
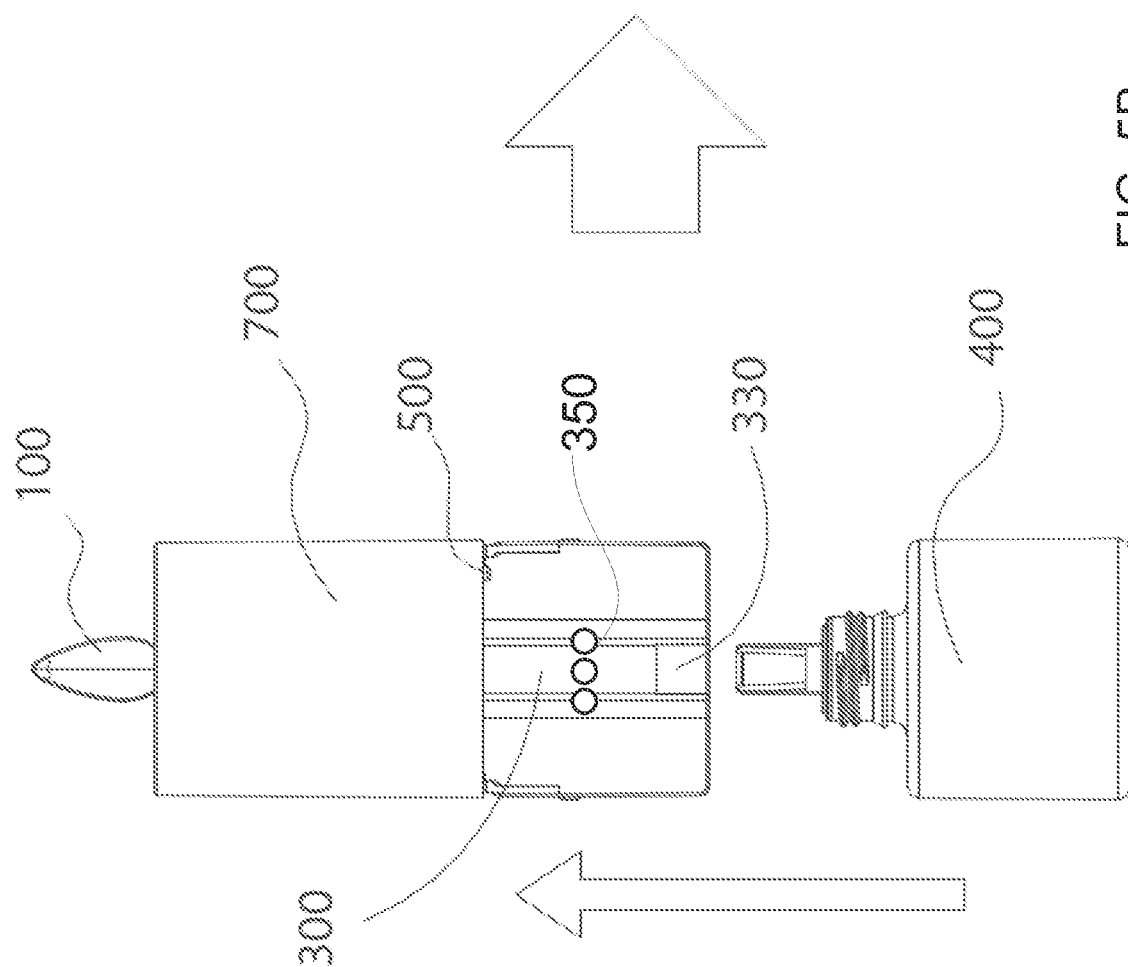
FIG. 5B illustrates another example installation process of installing a scent storage component of an example electronic candle in accordance with the present technology.

Referring to FIGS. 5A-5B, the scented electronic candle device can include a detection unit 500 configured to detect whether the scent storage component 400 is properly installed. In some embodiments, the detection unit 500 is connected to the control unit and can be triggered when the scent storage component 400 is installed on the mounting base 300, thereby obtaining a signal indicating that the scent storage component 400 is installed in place. The detection unit 500 can transmit the signal to the control unit so that the control unit can activate the heating unit 600 (as shown in FIGS. 4A-4B) to generate heat. The heat emitted from the heating unit 600 can promote the diffusion of the fragrance, thereby increasing the aromatherapy effect. The heating unit 600 can be a cement resistor or other types of heating units. The heating unit 600 can be installed on a heating unit bracket 610 (as shown in FIG. 4A), which can be installed on the mounting base 300.

The detection unit 500 can be implemented as various types of sensor devices, such as photoelectric sensors, trigger switches, etc. In some embodiments, the detection unit 500 can include a trigger switch. As shown in FIG. 5A, the detection unit 500 comprises a trigger switch can be located on an installation path of the scent storage component 400. When the scent storage component 400 is being installed to on the mounting base 300 along the installation path, the trigger switch is triggered. In some embodiments, the trigger switch is touch switch. The touch switch can be turned on or off by lightly touching the touch switch. A switch cap 510, as shown in FIG. 3A, can be installed on the touch switch.

In the embodiment shown in FIG. 5A, the detection unit 500 (e.g., a trigger switch) is arranged above the installation path of the scent storage component 400, During the installation process, the scent storage component 400 moves upward as shown by the arrow on the left side of FIG. 5A. When the scent storage component 400 is installed and coupled to the mounting base 300, the top of the scent storage component 400 touches the trigger switch 500, thereby triggering the generation of a signal that indicates the scent storage component 400 is in place. Alternatively, or in addition, the detection unit 500 can be arranged on the main body 310 of the mounting base 300. For example, the detection unit 500 positioned on the main body 310 can be triggered when it is pushed sideways (e.g., squeezed) by scent storage component 400 during installation. The detection unit 500 can include optical switches, electrical switches, magnetic switches to generate other types of signals (e.g., optical signals, electrical signals, magnetic signals, etc.).

The mounting base 300 and the scent storage component 400 can be coupled together in various ways. In some embodiments, the mounting base 300 includes a main body 310 and a top base 320 (as shown in FIG. 3A). The top base 320 protrudes from one side of the main body 310 to be coupled with the scent storage component 400 such that the scent storage component 400 is arranged side by side with the main body 310. In some embodiments, the scent storage component 400 can also be connected to the main body 310 of the mounting base 300 instead of the top base 320.

As shown in FIG. 5B, in some embodiments, the mounting base 300 includes one or more LEDs 350 (also illustrated in FIG. 3B) that are in connection with the control circuit. The one or more LEDs 350 can be controlled to emit different colors and/or change the colors of emitted light. After the mounting base 300 and the scent storage component 400 are coupled together, the one or more LEDs 350 are positioned behind the scented storage component 400 (e.g., transparent/translucent glass or plastic bottle) to emit different colors of light based on different settings (e.g., user preferences, time of the day, etc.).

In some embodiments, the main body 310 of the mounting base 300 includes an indicator light 330 to indicate the remaining amount of fragrance in the fragrance container 410. For example, the fragrance container 410 can be made of transparent or semi-transparent materials. The indicator light 330 is connected to the control unit configured to illuminate the body of the fragrance container 410 such that the amount of liquid fragrance in the fragrance container 410 is visible to the user. The indicator light 330 can be located close to the bottom of the fragrance container 410 or around the middle section of the fragrance container 410.

Referring to FIGS. 6-7, in some embodiments, the top part of the mounting base 300 is formed as a clamp to allow the top end 411 of the fragrance container 410 to be securely clamped to the mounting base 300. In some embodiments, the top part 320 includes a mounting hole 322 into which the top end 411 of the fragrance container 410 is inserted and securely clamped. As shown in FIG. 6, in some embodiments, the fragrance container 410 includes a liquid absorption channel 430 arranged at the opening of the fragrance container 410. The angle of the liquid absorption channel 430 with respect to a central axis of the fragrance container 410 can be adjusted. The arrangement of the liquid absorption channel 430 is configured to maximize the amount of fragrance drawn from the fragrance container 410 and to control the direction in which the fragrance is directed from the fragrance container 410.

Figure 10:
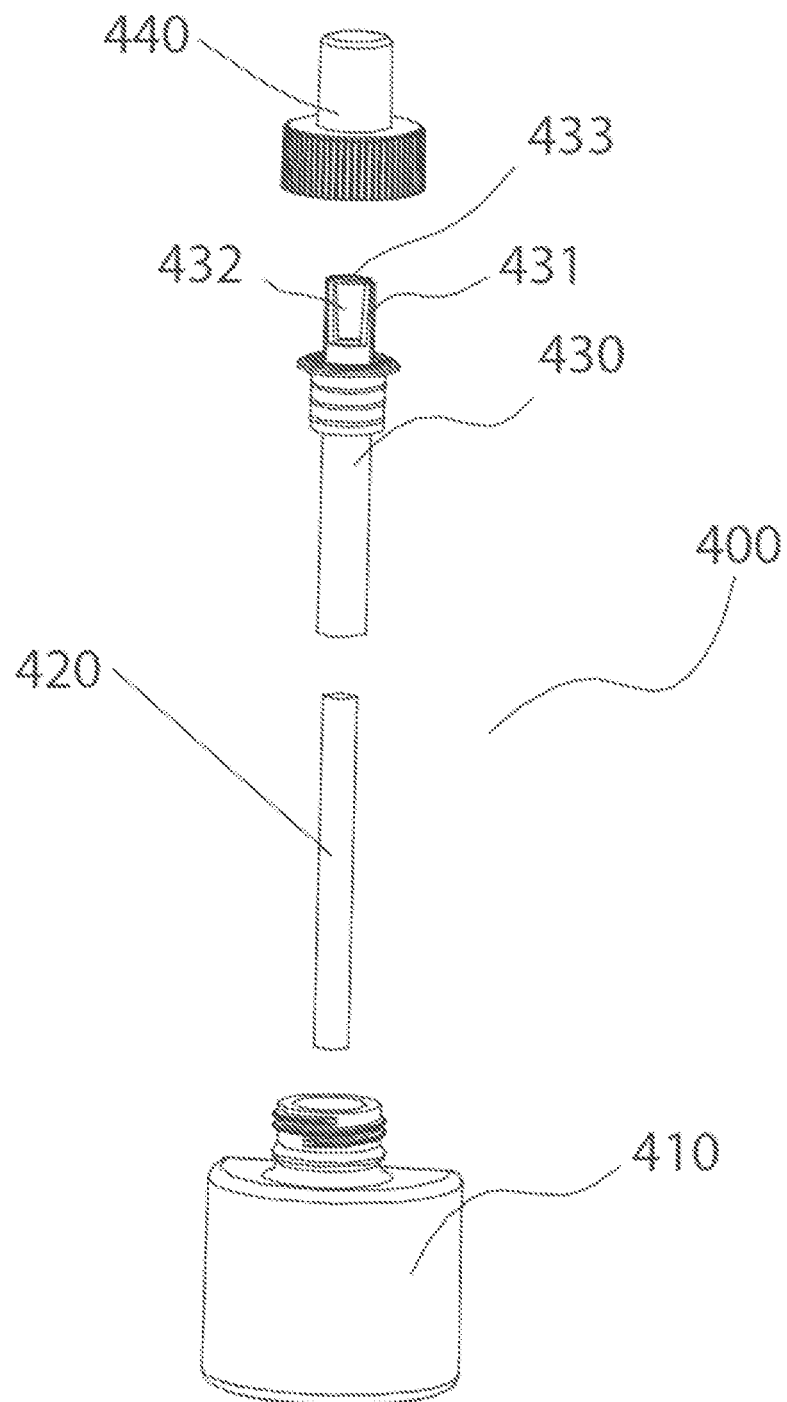
FIG. 10 illustrates a blow-up diagram of parts in a scent storage component of an example electronic candle in accordance with the present technology.
Figure 11:
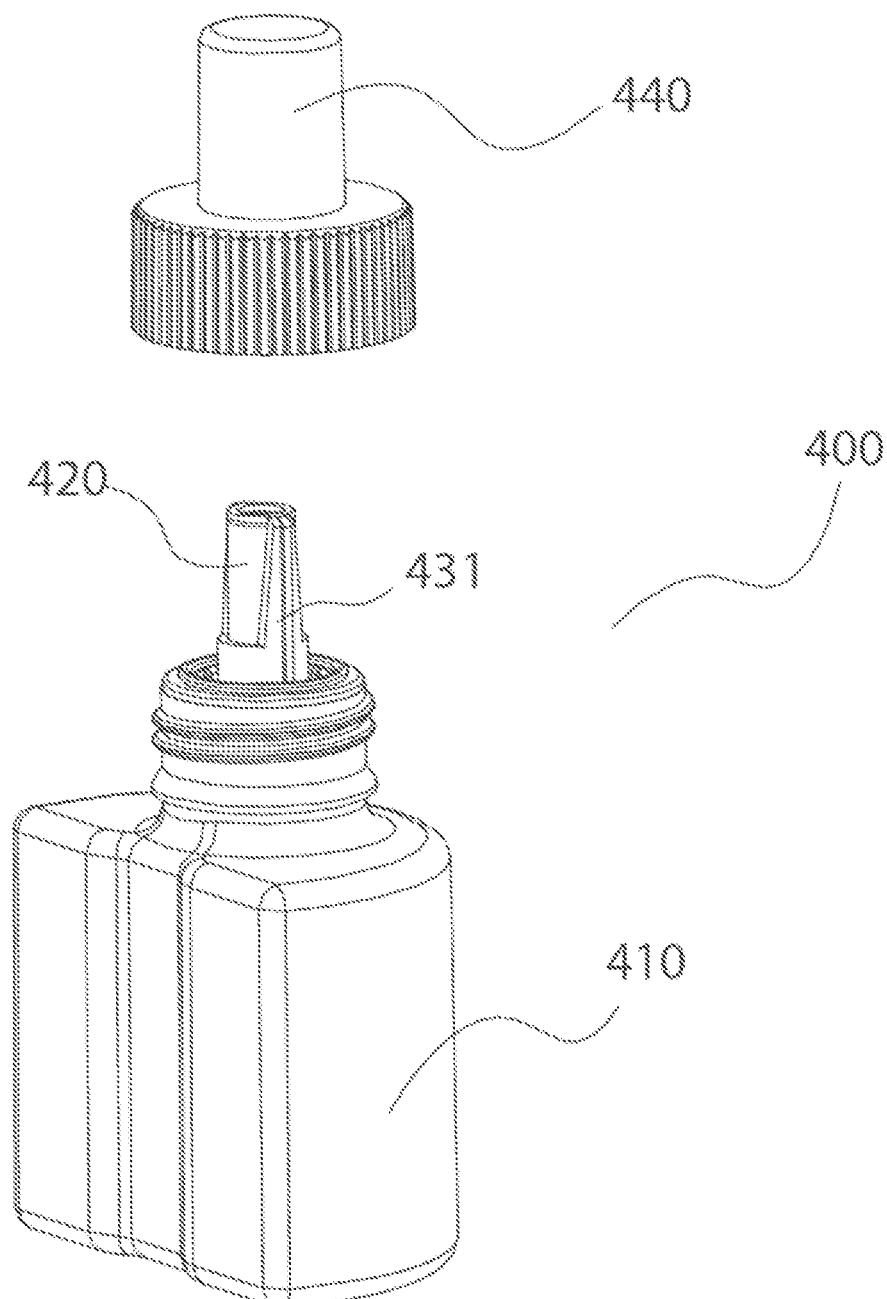
FIG. 11 illustrates an example scent storage component with a cap in accordance with the present technology.

In some embodiments, as shown in FIGS. 10-11, the liquid absorption channel 430 is installed at the opening of the fragrance container 410. The fragrance container 410 includes a cavity to hold the liquid fragrance. The liquid absorption channel 430 holds a liquid absorbing member 420 that extends into the cavity to draw the fragrance. The liquid absorption channel 430 is connected to a top end 431 that includes one or more fragrance dispersing ports 432 and 433 for dispersing fragrance. In some embodiments, the fragrance port 432 is provided on the side of the top end 431, and the fragrance port 433 is provided on the top of the top end 431. The top end 431 separates the liquid absorbing member 420 from other parts of the candle device. In some embodiments, the top end 431 includes a heat-resistant material such that, when the liquid absorbing member 420 and the absorption channel 430 are heated to accelerate the evaporation of the fragrance, the remaining parts of the candle are not affected by the heat. In some embodiments, the scent storage component 400 further includes a bottle cap 440 to prevent dust from collecting on the fragrance ports. The bottle cap can include small openings (e.g., on the side wall of the cap) to allow the fragrance to diffuse.

In some embodiments, the liquid absorbing member 420 includes a waterproof membrane (e.g., oiled paper, plastic wrap, etc.) and a core wick. The core wick can include absorbent materials such as cotton or woven felt. The waterproof membrane wraps around the side wall of the core wick, while the top and bottom ends of the wick are exposed to the fragrance and the air. The waterproof membrane can prevent excessive loss of fragrance when the electronic candle is knocked over or be turned sideways.

Figure 8:
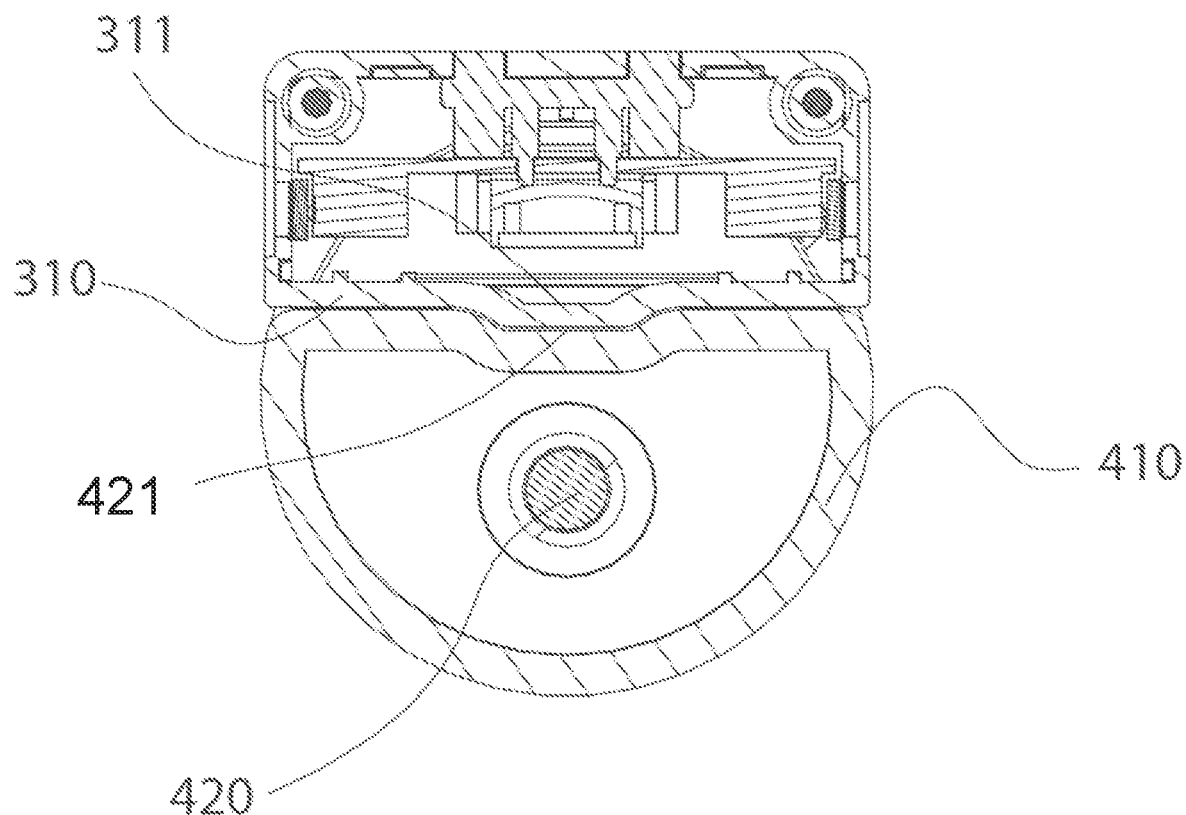
FIG. 8 illustrates a top view of a mounting base and a fragrance container of an example electronic candle in accordance with the present technology.

In some embodiments, as shown in FIG. 8, the main body 310 of the mounting base 300 has a limiting protrusion 311. The part of the fragrance container 410 facing the main body 310 includes a groove 421 that matches the limiting protrusion. Alternatively, or in addition, the main body 310 of the mounting base 300 has a limiting groove while the part of the fragrance container 410 facing the main body 310 includes a protrusion that matches the limiting groove. The limiting protrusion/groove and the corresponding groove/protrusion ensure that the fragrance container 410 is securely connected to the mounting base 300 and prevent the fragrance container 410 from shifting left or right from the mounting base 300.

Figure 9:
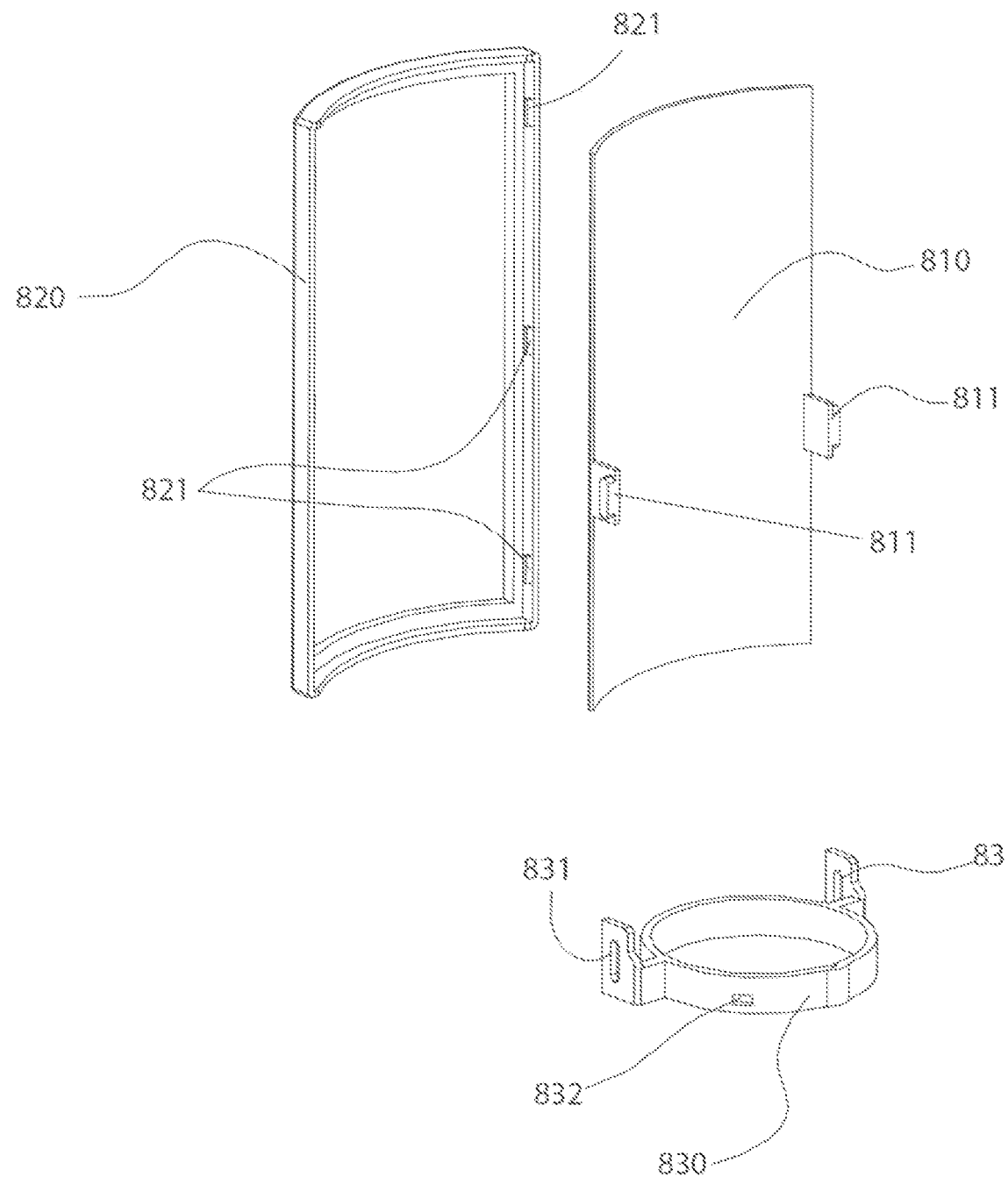
FIG. 9 illustrates an example element of an example electronic candle in accordance with the present technology.

In some embodiments, the scented electronic candle device can further include an element, as shown in FIG. 9, that is detachably mounted on the outer shell 700 or the mounting base 300. The element includes a transparent or semi-transparent sheet 810 that has various patterns printed thereon. When the light of the light-emitting unit 200 of the scented electronic candle device emits light through the transparent or semi-transparent sheet 810, various visual effects can be presented to users. The shape and/or size of the transparent or semi-transparent sheet 810 can be adapted based on users' preferences, such as shown in FIG. 3A.

Referring to FIG. 9, in some embodiments, a sheet holder 820 is provided to support the transparent or semi-transparent sheet 810. The sheet holder 820 has one or more fastening units 821 (e.g., buckles) on the left and/or right sides to allow the sheet 810 to be fastened on the sheet holders. The sheet 810 can further additional fastening units 811 (e.g., raised buckles or snap clips) on both sides to allow it to be removably attached to a snap ring 830. The snap ring 830 can be positioned around the outer shell 700 of the scented candle.

Figure 12:
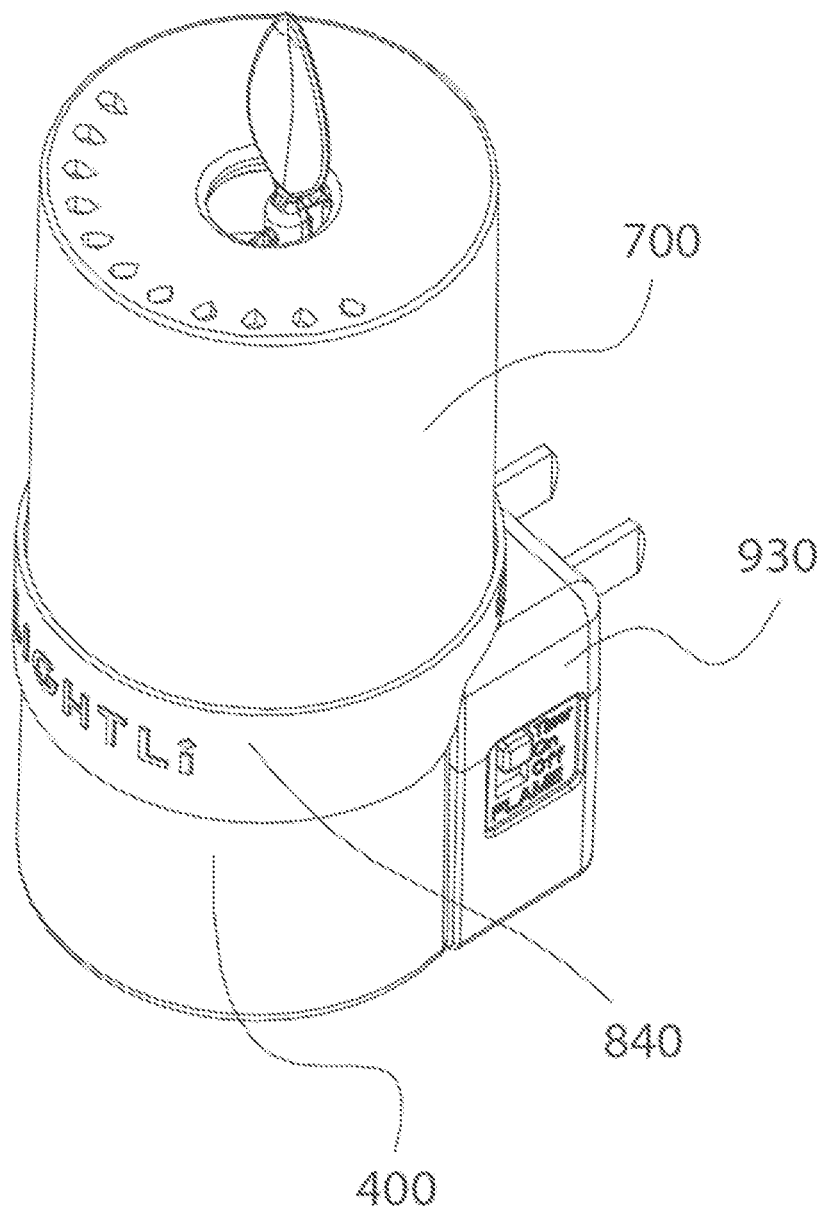
FIG. 12 illustrates an example electronic candle with a collar attached thereon in accordance with the present technology.

In some embodiments, as shown in FIG. 12, a collar 840 is can be detachably installed on the outer shell 700 or the mounting base 300. The collar 840 can be positioned to hide the connection between the outer shell 700 and the mounting base 300 (of any part of the mounting base 300 that is exposed). The collar 840 can be installed onto the outer shell 700 or the mounting base 300 via a fastening mechanism (e.g., snap clips or buckles). In some embodiments, the collar 840 can include printed logo of the scented electronic candle device or other elements. The shape and/or size of the collar 840 can also be adapted based on users' preferences, such as shown in FIG. 3A.

Furthermore, the scented electronic candle device includes a power plug assembly 930. The power plug assembly 930 can include one or more adaptors to adapt to universal interchangeable plugs, suitable for international usage. The power plug assembly 930 can be mounted to the mounting base 300 in a similar manner as mounting a screw (e.g., by rotating the power plug assembly 930). The power plug assembly 930 is connected to the control unit 1000. When the power plug assembly 930 is plugged into a power supply, the scented electronic candle device is provided power to operate. In some embodiments, the scented electronic candle device can function as a night light to provide aroma as well as soft lighting overnight.

In one example aspect, an electronic candle device includes an outer shell comprising one or more openings positioned at a top section of the outer shell and configured to allow a fragrance to exit to an ambient environment of the electronic candle. The outer shell further includes a central opening that allows a flame element to at least partially protrude through the central opening of the outer shell. The flame element is supported by a support structure to allow movement of the flame element that mimics a real flame. The device also includes a light emitting component positioned to emit a light onto the movable flame and a mounting base positioned below the movable flame element. At least part of the mounting base is enclosed by the outer shell. The device includes one or more guides coupled to the openings of the outer shell and a scent storage component removably coupled to the mounting base. The scent storage component includes a container to store a fragrance and an absorption member configured to draw the fragrance from the container to the ambient environment of the electronic candle through the mounting base, the one or more guides and the one or more openings of the outer shell.

In some embodiments, the support structure comprises a wire that supports the flame element. In some embodiments, the support structure comprises a bracket that supports the flame element. In some embodiments, the flame element comprises a magnet, and the device further includes a magnetic coil positioned below the flame element configured to alter a magnetic field to enable the movement of the flame element.

In some embodiments, the light emitting component comprises one or more light emitting diodes configured to emit a same color or different colors. In some embodiments, the light emitting component is positioned to illuminate the flame element from within the outer shell at an upward inclined angle. In some embodiments, the device further includes a lens positioned between the light emitting component and the flame element configured to direct the light from the light emitting component to the flame element.

In some embodiments, the device includes a heating element positioned in proximity to the absorption member. The heating element is configured to heat the fragrance as the fragrance passes through the absorption member. In some embodiments, the device includes a switch positioned along an installation path of the scent storage component. Upon the scent storage component being coupled to the mounting base, the switch is configured to generate a signal indicating that the scent storage component is installed in place. In some embodiments, the switch comprises a touch switch, an optical switch, an electrical switch, or a magnetic switch.

In some embodiments, the one or more guides are formed as a chamber within the mounting base that is connected to the one or more small openings of the outer shell. The absorption member comprises an absorption channel and a core wick, and a bottom end of the core wick is in contact with the fragrance held in the container and a top end of the core wick extends into the chamber. In some embodiments, the one or more guides further comprise tubes that are positioned at a side wall of the chamber within the mounting base.

In some embodiments, the core wick is wrapped with a water-resistance membrane configured to prevent a loss of the fragrance in case the electronic candle is tilted sideways. In some embodiments, the scent storage component comprises a top part positioned above the absorption member, the top part including one or more fragrance dispersing ports configured to disperse the fragrance from the absorption member through the mounting base. In some embodiments, the scent storage component further comprises a cap positioned above the one or more fragrance dispersing ports to prevent dust from collecting on the one or more fragrance dispersing ports.

In some embodiments, the mounting base comprises a protrusion, and wherein the container of the scent storage component comprises a groove that engages with the protrusion to allow the scent storage component to be securely installed to the mounting base. In some embodiments, the device further includes a control unit configured to control an operation of the device and a detachable power plug assembly mounted to the mounting base. The detachable power plug assembly is configured to connect to a power source to provide power to the control unit. In some embodiments, the detachable power plug assembly comprises an adaptor configured to interface with universal interchangeable plugs.

In some embodiments, the device includes a ring support positioned around the outer shell and a transparent or semi-transparent sheet coupled to the ring support. In some embodiments, the transparent or semi-transparent sheet comprises one or more designs printed thereon, the light emitting component is positioned within the outer shell, and the light emitted from the light emitting component is directed or refracted through the transparent or semi-transparent sheet. In some embodiments, the device includes a collar positioned close to a lower part of the outer shell and an upper part of the mounting.

In the present disclosure, the terms such as "first" and "second" are only for the purpose of illustration and they do not indicate or imply any relative importance. The term "a plurality of" means two or more, unless indicated otherwise explicitly. The term "connected" may refer to "connected directly" or "connected via an intermediate component". In the above description, it is to be noted that the terms indicating directions or positional relations, such as "up" and "down", indicates directions or positional relations as shown in the figures. They are for the purpose of simplifying description of the present disclosure, and do not indicate or imply that the device or unit in question should always be construed to have a particular direction or operate in a particular direction.

Some of the components or modules that are described in connection with the disclosed embodiments can be implemented as hardware, software, or combinations thereof. For example, a hardware implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application.

Some of the embodiments related to operations such as processing of signals or performing certain tasks and processes, described herein are described in the general context of methods or processes, which may be implemented at least in-part by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

The foregoing is merely illustrative of the preferred embodiments of the present disclosure and is not intended to limit the present disclosure. Various changes and modifications may be made by those skilled in the art. Any modifications, equivalent alternatives are improvements that are made without departing from the spirit and principles of the present disclosure are to be encompassed by the scope of the present disclosure.

What is claimed is:

1. An electronic night light, comprising:
   an outer shell comprising a central opening and a plurality of scent openings positioned at a top section of the outer shell configured to allow a fragrance to exit to an ambient environment of the electronic night light;
   a movable flame element at least partially protruding through the central opening of the outer shell, the movable flame element supported by a support structure to allow movement of the movable flame element that mimics a real flame;

a light emitting component positioned to emit a light onto the movable flame element;

a mounting base positioned below the movable flame element and coupled to the outer shell;

a plurality of guide tubes coupled to the plurality of scent openings of the outer shell;

a scent storage component removably coupled to the mounting base, the scent storage component comprising a container for storing the fragrance and an absorption member configured to draw the fragrance from the container to the ambient environment of the electronic night light through the mounting base, the plurality of guide tubes, and the plurality of scent openings of the outer shell; and a power plug assembly mounted to the mounting base, the power plug assembly configured to connect to a power source to provide power to the electronic night light.

2. The electronic night light of claim 1, wherein the support structure comprises a wire that supports the movable flame element.

3. The electronic night light of claim 1, wherein the movable flame element comprises a magnet, and the electronic night light further comprises:

a magnetic coil positioned below the movable flame element configured to alter a magnetic field to enable the movement of the movable flame element.

4. The electronic night light of claim 1, wherein the light emitting component comprises one or more light emitting diodes configured to emit a same color or different colors.

5. The electronic night light of claim 1, wherein the light emitting component is positioned to illuminate the movable flame element from within the outer shell at an upward inclined angle.

6. The electronic night light of claim 1, wherein the power plug assembly comprises an adaptor configured to interface with universal interchangeable plugs.

7. The electronic night light of claim 1, wherein the support structure comprises a bracket that supports the movable flame element.

8. The electronic night light of claim 1, comprising:

a curved sheet with one or more patterns printed thereon, the curved sheet coupled to the mounting base via fastening units on both sides of the curved sheet such that the mounting base and the scent storage component are not visible or only part of the scent storage component or the mounting base is visible.

9. The electronic night light of claim 1, further comprising:

a trigger sensor configured to turn the electronic night light on and off.

10. The electronic night light of claim 1, further comprising:

a heating element positioned in proximity to the absorption member, wherein the heating element is configured to heat the fragrance as the fragrance passes through the absorption member.

* * * * *